(12) United States Patent
Griffin et al.

(10) Patent No.: US 7,469,557 B2
(45) Date of Patent: Dec. 30, 2008

(54) METHOD FOR FORMING A CAPILLARY COLUMN FOR FILTERING, SEPARATION AND CONCENTRATION

(76) Inventors: Teresanne Griffin, 3437 E. Melody Dr., Phoenix, AZ (US) 85042; Stephen E. Griffin, 3437 E. Melody Dr., Phoenix, AZ (US) 85042

( * ) Notice: Subject to any disclaimer, the term of this patent is extended or adjusted under 35 U.S.C. 154(b) by 0 days.

(21) Appl. No.: 10/866,626

(22) Filed: Jun. 12, 2004

(65) Prior Publication Data
US 2006/0000238 A1    Jan. 5, 2006

(51) Int. Cl.
*C03B 23/207* (2006.01)
(52) U.S. Cl. ............................................... 65/55
(58) Field of Classification Search ............ 65/61, 65/32.2, 36, 42, 55, 57, 293; 210/198.2, 210/198.1
See application file for complete search history.

(56) References Cited

U.S. PATENT DOCUMENTS

| | | | |
|---|---|---|---|
| 3,319,403 A | * | 5/1967 | Rose et al. ............... 96/101 |
| 4,049,413 A | * | 9/1977 | French ..................... 65/392 |
| 4,116,836 A | | 9/1978 | DeAngelis ................ 210/198 |
| 4,263,030 A | * | 4/1981 | Kobayashi et al. ........ 65/426 |
| 5,951,731 A | * | 9/1999 | Tsunetomo et al. ....... 65/61 |

* cited by examiner

*Primary Examiner*—Eric Hug
*Assistant Examiner*—Queenie Dehghan

(57) ABSTRACT

The column according to the present invention provides greatly increased effective length and tortuosity, per unit length of column material, by providing a smooth or textured, tight radius helical channel or channels within a silica monolith. The capillary according to the present invention is useful in enabling fully automated massively parallel analyses, syntheses, separations and concentrations at reduced costs and higher speed as well as in immobilization, filtration, and miniaturization/acceleration/automation of classical instrumentation for practicality of general deployment in environmental threat monitoring and other applications.

8 Claims, 9 Drawing Sheets

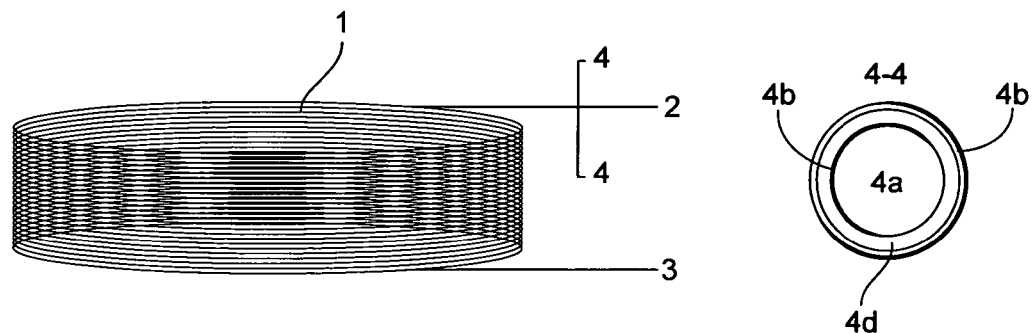
Fig. 1a
Prior Art
Fig. 1b
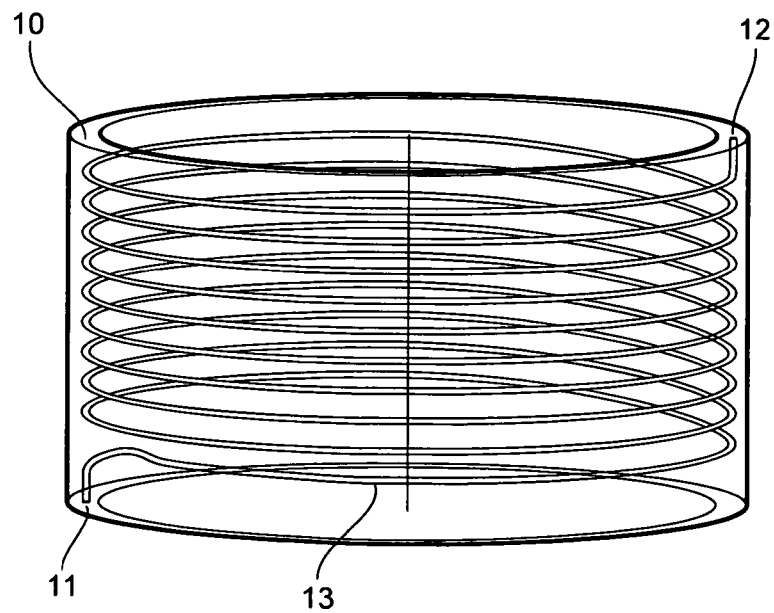
Fig. 2
Prior Art

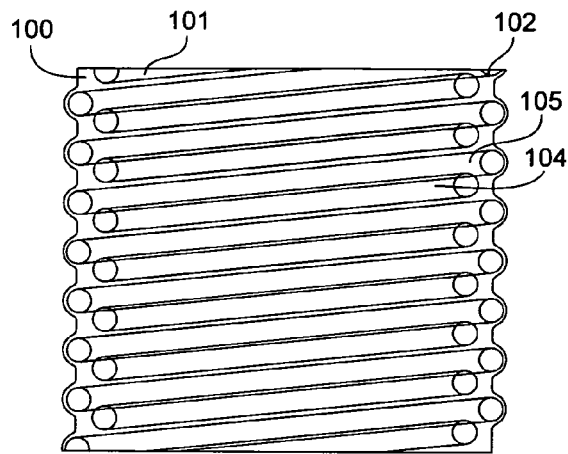
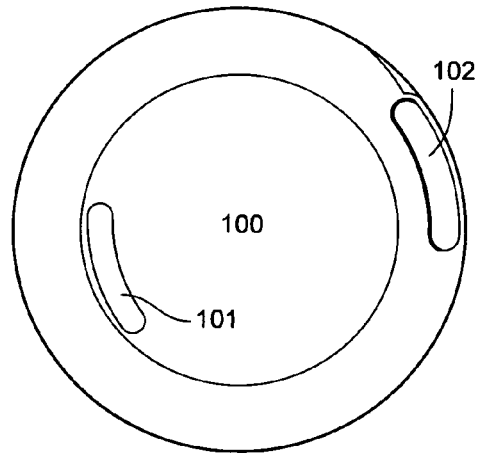
Fig. 10a            Fig. 10b
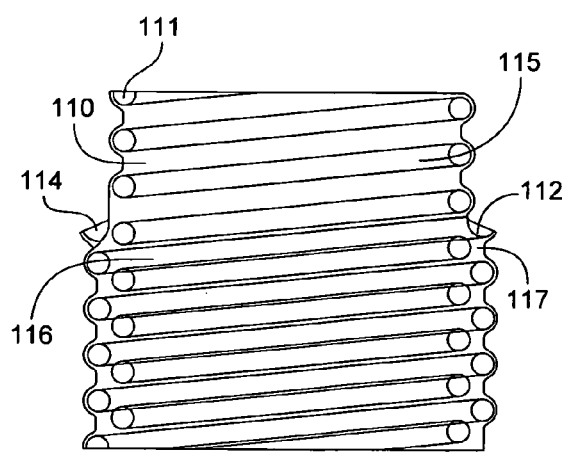
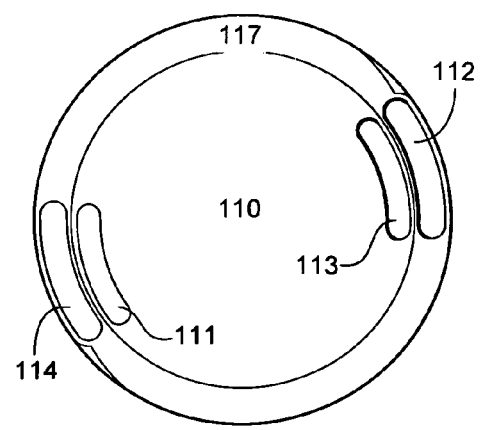
Fig. 11a            Fig. 11b

METHOD FOR FORMING A CAPILLARY COLUMN FOR FILTERING, SEPARATION AND CONCENTRATION

FIELD OF THE INVENTION

The present invention relates generally to separation sciences as applied to commerical analyses, portable chemical and biological threat detection, as well as filtering non-ideal samples with purification and concentration of target materials for further study, e.g., proteins and nucleic acids from cell lysates, and more specifically to capillary gas chromatography (GC), capillary electrophoresis (CE), capillary electro chromatography (CEC), capillary liquid chromatography (LC), affinity chromatography, capillary (or micro) high pressure liquid chromatography (HPLC) and related techniques, with additional applications in biotechnology such as isolation, concentration and delivery of target molecules (DNA, RNA, proteins, metabolites, complexes).

BACKGROUND OF THE INVENTION AND DESCRIPTION OF THE PRIOR ART

In separation sciences, many commercial instruments utilize polymer coated fused silica capillaries, with bare glass bore surfaces or with coated bore surfaces (WCOT or wall coated open tubular) and packed columns. The most common fused silica capillaries used, such as in capillary GC, are coated (buffered) with a polyimide and having bore dimensions from approximately 0.15 mm to 1.00 mm, outer diameters (polymer) from approximately 0.25 mm to 1.25 mm, and lengths from several meters to one hundred meters. In CE and related techniques, capillary LC and capillary HPLC, capillary bores range from approximately 0.002 mm to 0.200 mm with outer diameters of 0.150 to 0.375 mm and are used in lengths from a few centimeters up to a meter. Capillaries may also find applications in "micro-plumbing" for manipulating very small samples.

Much of separation sciences is based upon differential partition of compounds in mixtures of liquids, vapors or gases between the "mobile phase" and "stationary phase" within the capillary column. Components in a mixture that adhere, adsorb or absorb less readily in stationary phase are transported more rapidly along the column than are components that are strongly absorbed, adhered, dissolved or otherwise bound to the stationary phase.

In capillary electrophoresis and some related methods, capillaries need not be coated or packed to effect separations as the mechanism of separation is based upon mass and charge and/or tertiary structure of the species in the mixture, typically macromolecules, but coatings and packed columns do offer additional specificity and control of mobility mechanisms and conditions. In liquid chromatography, separations based upon partitioning between stationary and mobile phases is the rule, but with liquid mobile phase and solid or liquid stationary phase, additional partitioning mechanisms may be exploited, e.g., antibody affinity. In gas chromatography, as a rule, separations are based upon differential partitioning between a stationary liquid phase and a mobile, inert gas phase.

These common techniques and more esoteric separation and concentration schemes exploit fused silica capillary as column base material, owing to the relatively low cost, high tensile strength and flexibility and generally inert chemical character of the material. While a boon for advancing separation techniques in speed, resolution and ability to handle extremely small samples, fused silica capillary does present several problems and limitations. Problems in silica capillary separations are myriad and differ somewhat depending upon the technique in question. Some examples of these problems are the necessity to tightly coil long columns in or on cages for handling and mounting in instrument ovens, upper processing and use temperature limits imposed by the polymer buffers' liability to oxidation, irreproducible sample loading in tiny capillary bores, fragility of on-column detection windows (devoid of polymer protection), lack of efficient and convenient interface with larger scale laboratory glassware and instruments and limited available surface area and tortuosity in the smooth bore.

In GC, many separations are performed with temperature programs wherein the entire column is raised in temperature over time to aid in eluting sequentially less volatile compounds. Efforts to speed such separations, where temperature program cycles may require over an hour to complete, depend upon the ability to raise and lower column temperatures more rapidly and also upon the upper temperature limit of the column. While stationary phase polymers capable of transient temperatures above 400° C. do exist, the buffer coatings that protect the flexible capillary generally degrade beginning at about 350° C., effectively limiting the upper use capacity of capillary columns. In addition, some processes used to modify the bore surface for binding stationary phase are less effective than they could be due to the sub optimal upper use and processing temperature limit of commercial fused silica capillary. A silica capillary column that is rugged enough for general handling without requiring polymer buffers has the distinct advantage of having upper use limits higher than any known column treatment process requirement or polymer stationary phase degradation temperature. Current means of circumventing the upper use temperature limit involve use of metal-coated silica capillaries, with limited success and practicality.

Additionally, the current ubiquitous coils of capillary within the column oven make differential column heating along the axis impractical: the entire column is at the same temperature at the same time. Additional separations may be addressed or current separations may be accelerated or resolution improved if columns could be held or ramped at different temperatures along the separations axis.

Column heating and cooling is currently inefficient and slow, owing to the necessity of heating and cooling the entire oven volume as opposed to the relatively small column volume. Developments have recently been made in reducing this problem, e.g. heating the capillary coating by radio frequency energy (RF), direct electric heating via a resistive heating element wound about the capillary length, but all have limitations and increased costs associated with them. U.S. Pat. No. 4,116,836 issued to DeAngelis discloses a packed monolithic hollow cylinder column of generally standard scale, with a helical or sinusoidal path within a cylinder wall, formed by fusion of compound glasses about a sacrificial mandrel or through fusion of plates with aligned channels. While interesting and likely of some value, this large monolithic approach to the problems of silica capillary in GC remains massive and extremely costly to produce.

Increasing the bore surface area in capillaries, upon which to immobilize stationary phase, benefits efficiency (as measured by speed or resolution or height equivalent to theoretical plate) but most means of increasing bore surface area also degrade performance by increasing eddy diffision (turbulent mixing). Any means whereby surface area might be increased without adversely increasing diffusion or restricting flow improves efficiency.

In other techniques, such as purification of proteins by capillary affinity chromatography, turbulent flow of the liquid mobile phase aids in insuring contact with target compound-specific wall coatings in relatively short interaction lengths, aiding efficiency. Some researchers adhere to the practice of tightly coiling capillary columns to impart turbulent flow within the liquid channel, insuring better probability of contact between target species and the coating. But tightly coiling capillary leads to new problems such as physical column containment and column fracture due to excessive bend stress (compression and tension) and the minimum radii to which it is practical to coil capillary are quite limited, e.g. a 200 µm inner diameter by 330 µm glass outer diameter capillary cannot safely be coiled tighter than a diameter of approximately 3.3 centimeters such that the maximum angle circumscribed by a centimeter of capillary is approximately 42°. A capillary that could offer higher tortuosity and/or turbulent flow without high stress would be a great advantage, for improved efficiency as well as for compaction to enable address of all wells of a microtiter plate (MTP) simultaneously, for example.

Much research and development has been performed in production and use of "lab-on-a-chip" type technologies in recent years. Devices encapsulating channels within polymer or glass monoliths are provided as alternatives to cylindrical capillary, for considerations of space and speed and for providing multi-dimensional separations, selectable on-column sample "loops" and ease if interface to optical and electrochemical detection schemes. These wafer-based, planar technologies suffer from difficulty in sample loading and recovery—often referred to as "real-world interface" problems—and are typically costly to produce, particularly in small production runs. Planar devices are rarely made of silica, even though silica is extremely attractive for optical and chemical properties, because of the great difficulty and cost of patterning and fusing layers of silica. By providing such microfluidic circuits on cylindrical substrates or monoliths, patterning and fusion are greatly simplified and standard, or slightly modified, flexible capillary interface schemes are compatible with cylindrical "lab-on-a-chip" technology. Several orders of magnitude in cost reductions and increased speed in analyses are possible with the disclosed technology.

Beyond the more obvious surface area to volume ratio alterations provided by multilumen silica capillary, additional applications, ranging from photonic bandgap-based waveguides (so-called photonic crystals) to filters are possible that may better be addressed in direct laser formation rather than draw of large preformed structures (preforms). The dimensional reduction ratios of freely drawn glass products limit possible dimensions in products produced and free draw is highly inefficient for low volume production.

SUMMARY OF THE INVENTION

The invention claimed and described herein comprises capillaries with other than straight cylindrical bores, providing myriad alternatives to capillary coiling, packing, packing retention, and the like. Among the objects of the present invention are the following:

To provide a new and useful capillary geometry for eliminating the necessity for costly and problematic polymer, metallic or other buffer coatings;

To provide a new and useful capillary geometry for increasing tortuosity without column coiling or packing;

To provide a new and useful capillary geometry for altering surface to volume ratios without adversely affecting eddy diffusion;

To provide a new and useful capillary geometry for retaining column packing with minimal flow restriction or disruption to the separations mechanism;

To provide a new and useful capillary geometry providing alternative coupling schemes to optical and electrochemical detection;

To provide a new and useful capillary geometry for simplification of interface to the "real world" for sample preparation and handling;

To provide a new and useful capillary geometry for filtering unwanted contaminants from samples with minimal flow restriction or disruption to the separations mechanism while providing simple, visual inspection capacity;

To provide a new and useful capillary geometry permitting differential temperature maintenance or cycling along capillary separation axes;

To provide a new and useful capillary geometry for permitting more rapid, accurate and precise thermal change in whole columns or specific column sections;

To provide a new and useful capillary geometry for splitting flow in capillary for multi-dimensional analyses, redundant detection, differential detection or sampling and alteration of carrier to sample population distribution;

To provide a new and useful capillary geometry reducing surface forces on delicate structures in pressure or vacuum immobilization applications;

To provide a new and useful capillary geometry integrating one or more of the above functions within a single monolithic structure; and To provide new and useful methods of producing new capillary geometries and components based thereupon.

The novel features that are considered characteristic of the invention are set forth with particularity in the appended claims. The invention itself, however, both as to its structure and its operation together with the additional objects and advantages thereof will best be understood from the following description of the preferred embodiment of the present invention. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments of the invention is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. § 112, paragraph 6. Moreover, even if the provisions of 35 U.S.C. § 112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

BRIEF DESCRIPTION OF THE DRAWINGS

FIG. 1a is a perspective diagram of prior art: a standard capillary gas chromatography column.

FIG. 1b is an illustration of the capillary cross-section viewed along line 4-4.

FIG. 2 is a perspective diagram of prior art: helical passage within a glass monolith.

FIG. 3a depicts a partial section of the new art helical passage within a glass monolith.

FIG. 3b depicts a partial section of the new art helical passage within a glass monolith that is orthogonal to FIG. 3a.

FIG. 10 depicts two orthogonal partial sections for another possible multilumen capillary structure in a single monolith: single helices in different layers.

FIG. 11 depicts two orthogonal partial sections for another possible multilumen capillary structure in a single monolith with isolated ports: single helices in different layers with openings in different planes.

DESCRIPTION OF THE PREFERRED EMBODIMENT

The present invention is useful for performing a myriad of separation techniques.

Describing the preferred manufacturing method is useful in later visualization of the myriad alternative embodiments for the new art devices. While the preferred manufacturing method enables most configurations envisioned, additional processing techniques may be required or preferred in producing some configurations and are considered to fall within the scope of the present invention.

Figures 4A, 4B:
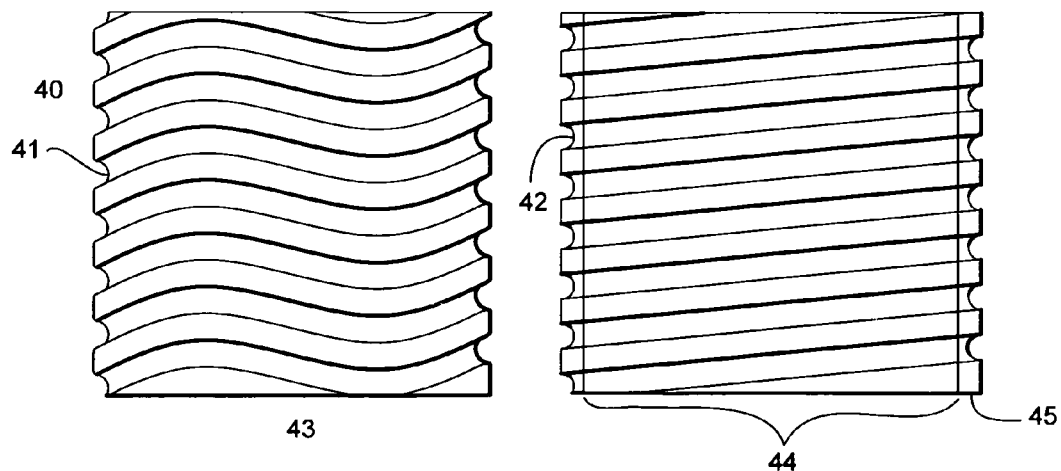
FIG. 4a is a side view in partial section of a simple helix channel pattern.
FIG. 4b is a side view in partial section of a wavy helix channel pattern.
Figure 4C:
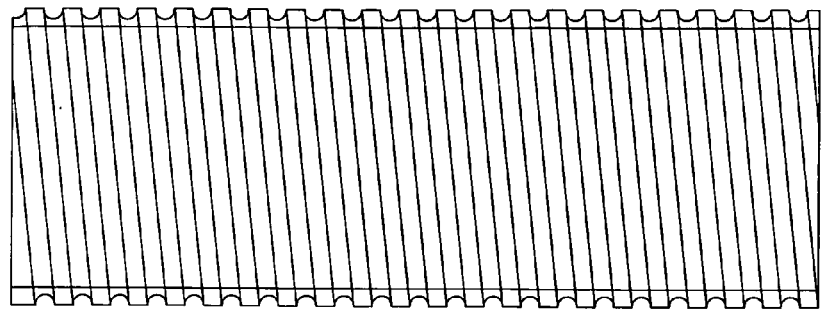
FIG. 4c-f are side views in partial section illustrating the basic steps in forming a circular cross-section, single channel helical monolithic capillary.
Figure 4D:
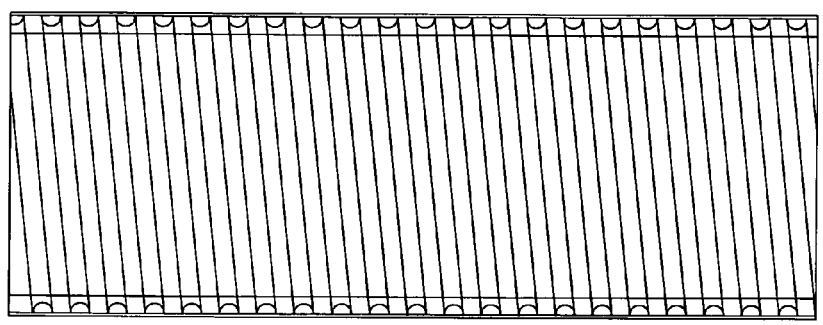
Figure 4E:
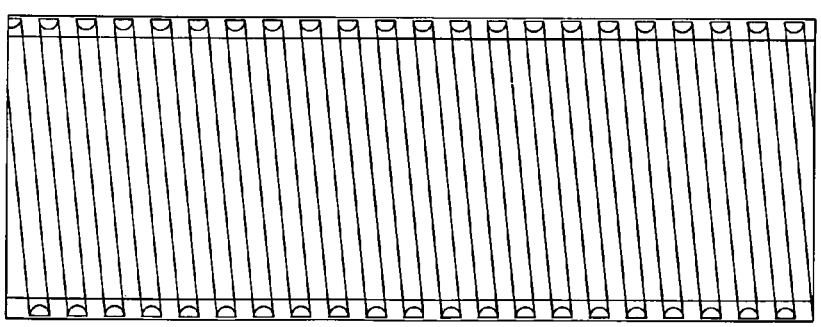
Figure 4F:
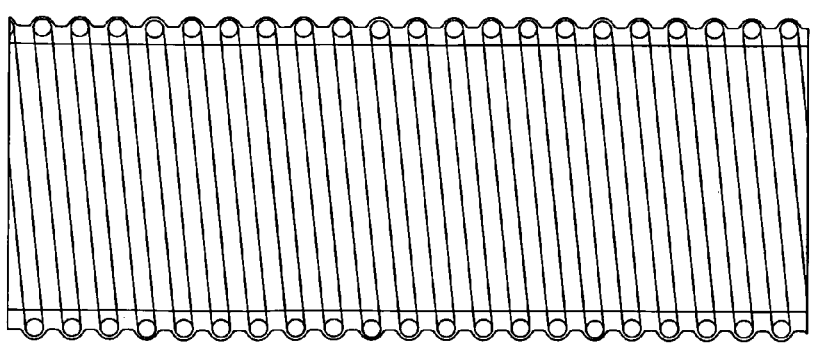

The simplest embodiment of the present invention is produced from rod 43 and tube stock 44, preferably fused silica, as depicted in FIGS. 4a and 4b, and assembly of which is depicted in FIG. 4c through FIG. 4f. The rod 43 or tube 44 is mounted in a precise collet within a Jeweler's lathe spindle or suspended between two aligned spindles. A laser is focused and indexed along the axis of the rod 43 under rotation, forming a helical groove 42 with the desired depth, width and pitch—in essence a screw thread is formed on a rod 43. A thin wall tube 46, just larger in bore than the rod 43 is slipped over the now threaded rod 43 or tube 44. Under rotation with the laser "defocused" (focal point located other than on the tube/rod outer diameter 45) so as to just melt the thin wall cover tube 46, the beam passes over the sleeved threaded section once more, fusing the thin wall sleeve 46 to the peaks of the channels in the rod 43 or tube 44. The cross-sectional geometry of the channel is dependent upon the beam profile used to form the channels and can vary from triangular to hemispherical to essentially square. If a round cross-section is desirable, the hemispherical channel can be matched following the channel closure (sleeve fusion) by passing the device through the laser beam a third time, with internal pressure applied to the hemispherical channel to expand the thin wall to a matching profile. Coiled channels are easily effected to circumscribe >1000° in a single centimeter of equivalent linear, 200 μm bore capillary length: a 25-fold increase over prior art.

It is readily apparent that multiple, parallel channels may be formed in a similar manner as the single channel. It is also readily apparent that channels can be made to cross to form a labyrinth channel. By controlling channel depths and pitches, one may produce a highly divided channel with varying degrees of surface area to channel volume, useful in mixing, filtering and other turbulent flow based operations or in separations and extractions that are improved by increased interaction of fluid or gas flow and the surfaces. It is also apparent that the depth, diameter and other dimensional features of a channel or channels may be varied along the length of the monolith, providing mechanisms for additional variable in separations, e.g. variable potential different along the length of a CE capillary.

Following this through another stage, a new channel or channels may be formed on the new outer diameter produced by the sleeve on the rod and this channel(s) may be closed by a second sleeving operation. The channeling and sleeving operations may be repeated, ad infinitum, to produce highly "porous" monoliths with low to high tortuosity. Rather than a simple helix, channels may be formed in a variety of patterns, e.g. the wavy helix (FIG. 4a, 41). Layered channels can be joined with holes through sleeves or by other means. Parallel channels in one layer can remain isolated or may be joined in any combination at any place within the structure prior to or, within limits, after fusion of the encapsulating sleeve(s). The rotational direction can be reversed and the laser can be modulated and synchronized with rotation and axial index to produce complex circuits in a single layer or in multiple layers with and without communication between them. Layers of channels need not be the same length; by making some layers shorter and longer, a simple method of layer isolation is enabled (FIG. 16).

Figure 15:
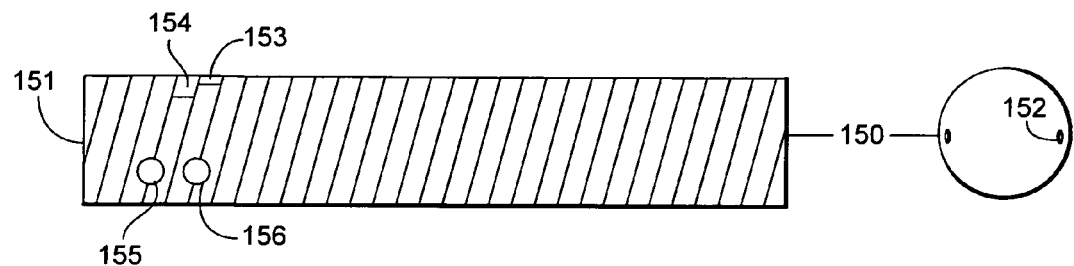
FIG. 15 is two orthogonal views in partial section comparable to a a "standard" microfluidic device or 'lab-on-a-chip'.

Channels can be modified post encapsulation as in FIG. 15, by restricting or collapsing a portion or portions of channels 152 and by joining channels 153. Connections to channels within the monolithic silica structures produced may be accomplished by a variety of means, e.g., perforations through encapsulating walls 156 or by cutting the monolith. An endless variety of fluidic circuits, single channel and multiple channel devices may be produced with no tooling changes, permitting low cost and rapid production of prototypes for testing.

Figure 16:
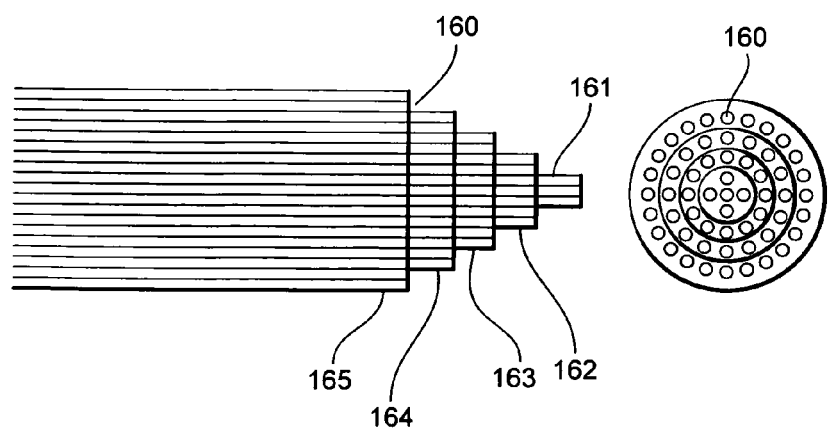
FIG. 16 is two orthogonal partial sections depicting a simple, multilayer, multi-axial lumen capillary arrangement analogous to a photonic crystal.

If channels are made straight, parallel to the rod axis (or hollow tube starting material) with repeated sleeving and channel formation operations, semi-microscopic to macroscopic structures resembling photonic crystal fibers may be formed as depicted in FIG. 16. In the figure, a heavy wall, single axial channel capillary of original diameter 161 is laser machined with four axial grooves. These grooves are converted into channels by fusing a thin wall capillary of outer diameter 162 over the grooved monolith. The new structure is again machined and sleeves with 163, 164, and 165, ad infinitum, to form repeat layers of axial channels in layers of glass. In this depiction, layers added subsequent to the primary layer are made shorter than the layers before, providing steps in diameter upon which seals can be made to address individual layers separately, or even individual channels 160 separately. Short sections of rigid photonic crystal fiber, or even photonic crystal preforms, may be precisely produced by this method or by the multiple helices variation, or perhaps even the wavy helices variation, depending upon the performance desired.

Useful structures may be thermally drawn to smaller diameters for additional applications, as micro sieves for filtration, nebulization, force distribution and other applications, independently or incorporated within other structures.

Other methods of forming, encapsulating channels, expanding, terminating and interconnecting channels may be used in place of laser formation, fusion, collapse and joining, where useful.

The preferred embodiment is similar in concept to prior art, illustrated in FIG. 2, except for materials of construction, assembly method and scale. The DeAngelis helix is a glass monolith that, while interesting in concept, has some apparent fundamental problems in these same areas: materials of construction, processing and size/mass. While the DeAngelis monolithic approach to forming a column did have apparent advantages in gross strength, the mass was likely somewhat unwieldy while the envisioned potential for improved thermal cycling, separations efficiency and viable column length was readily eclipsed by fused silica capillary materials.

The present invention is on a scale very similar to standard fused silica capillary—in possible effective column lengths and in total column mass—permitting use in the installed base of instruments as well as permitting development of new instruments that are smaller, consume much less power, perform separations faster and permit gradient column heating as a new variable in analytical methods development. Dimensions compatible with CE and LC, in addition to GC, are also easily addressed with a new set of fundamental advantages offered by the new column architectures and features.

Advantages offered by the present invention are described by application, beginning with GC.

The largest bore and longest length commerical GC column is approximately 0.53 mm bore by 100 m long (0.700 mm total strand diameter in a coil of about 8" diameter for about 160 coils height). The best arrangement for such a column is a single helix with each strand separated from the adjacent strands by a space to permit even airflow during heating and cooling. FIGS. 1a and 1b depict such a column where 1 is the hollow cylindrical space defined by the coil through which controlled temperature air is blown, 2 and 3 are the inlet and outlet, respectively and section 4-4 is a cross-section of the capillary strand where 4a is the open bore, 4b is the surface upon which stationary phase is deposited (generally from 0.0001 to 0.005 mm thick), 4c is the fused silica and 4d is the polyimide buffer. Such a column would be approximately 9 inches tall in the largest and longest variation, too tall to fit in some column ovens. Some columns are woven on cages with odd numbers of posts such that the column overlap is minimized to crossover points in the weave. This scheme reduces the column height to a more manageable, ~4.5 inches, height, but these large columns, and other columns, are commonly less than optimally wound, with bundled overlapping coils. FIG. 2 is the prior art helix in glass monolith on the same dimensional scale as the standard coil column in FIG. 1b with 10 being the monolithic hollow cylinder, 11 and 12 being the inlet and outlet, respectively, and 13 being the helical path captured in the monolithic structure.

While uniform spacing of the channels is provided by the prior art (FIG. 2), the structure does not permit the larger column construct analogs to that above, as the simple geometry is limiting. In addition, while uniform heating is accomplished for the prior art monolith, by virtue of the large hollow cylindrical form, the mass of the object is far larger than the mass of a modem capillary column and this larger mass resists rapid temperature changes. In addition, interfaces with the inlet and outlet on the monolith ends are not easily accomplished with current connection components due to the large scale and mass of the device.

Figures 3A, 3B:
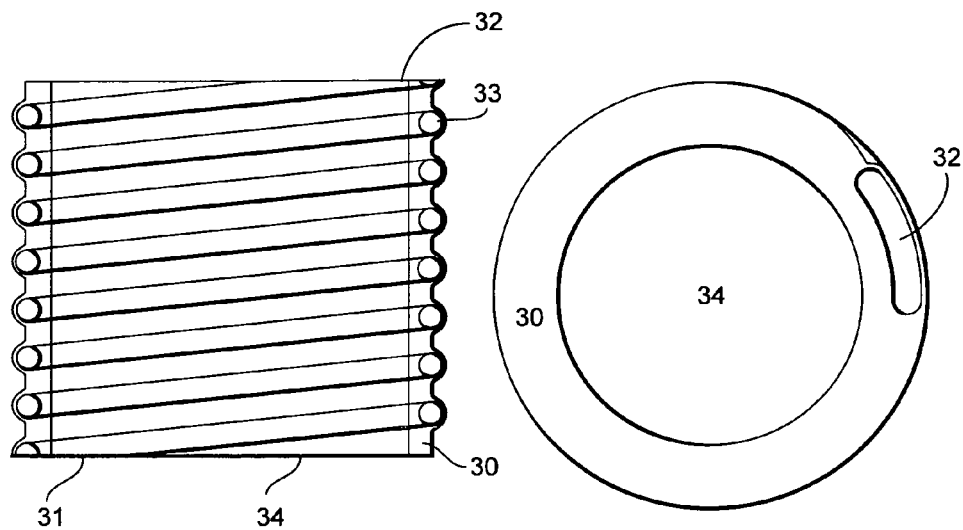
Figure 6:
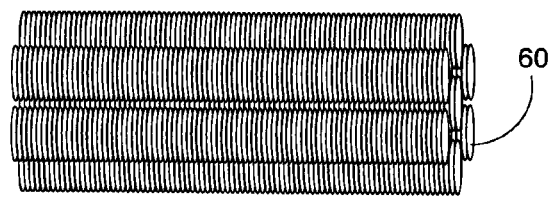
FIG. 6 is a perspective view of one possible arrangement for combining multiple sections of the basic helical monolith structure for increased effective length or for forming a multilumen column capable of independent tasks in one instrument.
Figure 8:
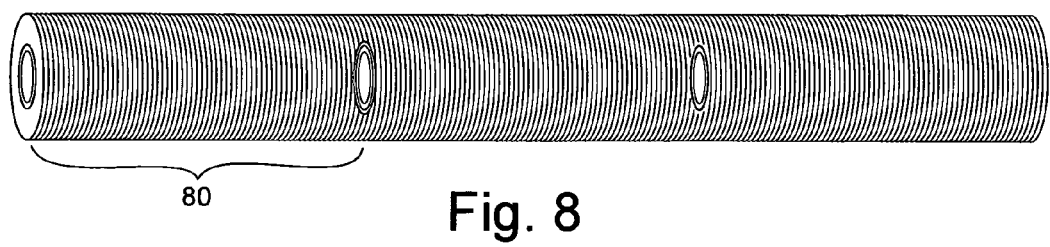
FIG. 8 is a perspective view of a possible arrangement of capillary column elements for variable effective length management.

In contrast to the prior art, the present invention comprises various arrangements of the simple helical elements depicted in FIG. 3 where 30 is the thin wall of a silica tube with bore 34, upon which a single helical channel is formed 33. Openings at each end, 31 and 32, appear elongated due to the high approach angle to the flat end surfaces. One possible structure for GC, permitting free airflow for temperature programming, is composed of hex packs of these elements formed on hollow cylinders (for air passage), coupled together. FIG. 6 depicts this "honeycomb" arrangement 60. Simple cartridge heaters could be used for direct thermal control of the column elements, individually or in unison. Another possible structure is composed of multiple pass cylinders: a cylinder with a helical path traversing from end to end, then reversing on another level to traverse end to end again, reverse and traverse, until the desired length is provided in multiple concentric helices, or a helical version of the layered, axial channel monolith depicted in FIG. 15. These "onion layer" columns may then be stacked to provide independent sections that may be held at different temperatures, forming a gradient as in FIG. 8 where 80 is one independently controlled section of the overall device.

Figure 7:
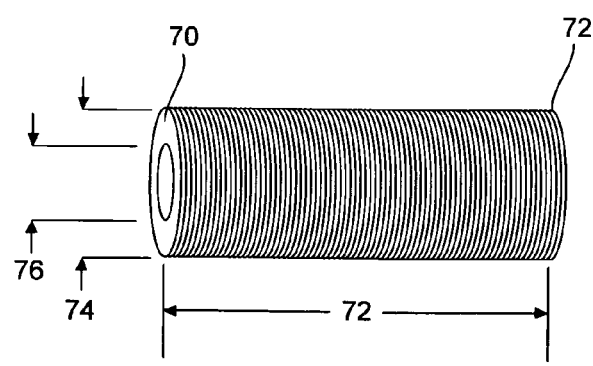
FIG. 7 is a perspective view of a single section of new art GC-type capillary chemically analogous to current art but highly compressed in dimensions.

For a typical fused silica capillary GC column, e.g. some 40-meters length of 320 µm bore by 435 µm polyimide OD capillary, wound in a stainless steel cage some 8 inches in diameter and 1.5 inches tall, an new art analog could be accomplished beginning in the center, at 10mm mean coil diameter with a 0.32 mm channel at 0.5 mm pitch by 5 cm high (314 cm equivalent linear length), reverse to the next level at 0.5 mm spacing for 11 mm mean diameter on 0.5 mm pitch (346 cm effective length), reverse to the next level at the same spacing for a third traverse of 377 cm . . . 408 cm on the forth pass, 440 cm, 471 cm, 502 cm, 534 cm, and 565 cm at 18 mm mean diameter of coil, for total column dimensions depicted in FIG. 7: an inlet 70, 320 μm in bore diameter, near the center of the inner diameter 76 of the resulting monolith at approximately 9.8 mm, communicates with the outlet 72 near the outer diameter 74 of under 2 cm after traveling the 5 cm length of the cylinder 78 several times in layered helices. To extend the column length to 80-meters, two sections could simply be fused together on the axis the cylindrical monolith with interconnection through the central bore, as in FIG. 8.

Addressing larger, longer columns is a bit more problematic, although well within the dimensional constraints of current installed commerical equipment; by increasing the number of helical passes per section, increasing the starting diameter for the inner coils or lengthening the section somewhat. very long, large bore monolithic column may be formed in a variety of geometries.

Heavy wall glass cylinder monoliths are slow to change in temperature; bad for high speed programmed temperature applications, but excellent for isothermal work. For rapid temperature programming, one is aided by physically reducing the column oven dimensions, minimizing the mass of the column and maximizing the air (or fluid) flow around the column or by providing alternative, more direct heating (recent prior art includes RF heating trough a special, doped polyimide coating). The invention described herein accomplishes two of these objectives—dimension reduction and providing alternative, more direct heating (with possible thermal feedback for precise control). Many rapid temperature program applications utilize relatively short columns of small-bore dimensions, making the mass reduction less of an issue. Temperature program in combination with gradient heating of the column may well further reduce the column length/mass requirements.

Even at moderate column bore, approximately 100-fold length compression is offered by a single helix on a 10 mm mean diameter is possible. On 25-mm mean diameter (roughly 1 inch), a 250 μm bore on 350 μm pitch provides roughly 2.25 m of effective length per centimeter column length such that a common 10-m helical column would occupy a hollow cylinder monolith of roughly 24.5 mm ID by 25.5 mm OD by 5 cm length—approximately 2 cubic centimeters of silica occupying just over 35 cubic centimeters total space. For very compact applications, such a cylinder could be flattened to 2 mm thickness by about 4 cm width by 5 cm length: about the same as a half credit card. With modification and miniaturization of sample introduction and gas handling, such a column enables production of hand-held, battery or solar powered gas chromatographs that could incorporate MEMS-based mass spectrometric detection capable of semi-continuous to continuous sampling of air (or fluids), e.g. for indications of terror weapons.

Figure 5:
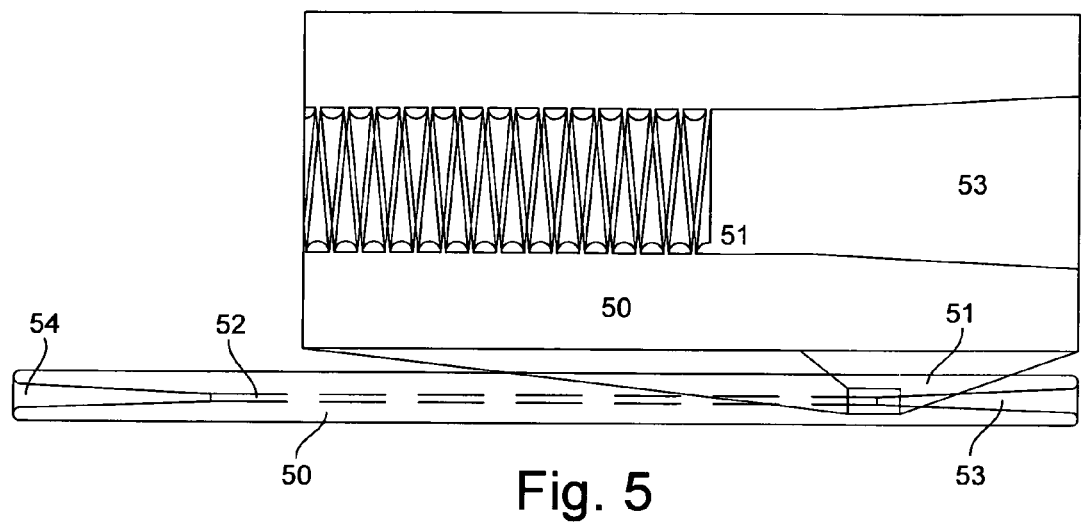
FIG. 5 is a side view in partial section with expanded detail of a component based upon the new art: a GC guard column.

In more immediate GC applications such compressed effective length devices find immediate utility as guard columns and retention gaps illustrated in FIG. 5. In the guard column prior art, a relatively short (0.5 to 1.0 m) section of standard fused silica capillary is connected between the injection port and the separation column by means of "press-fit" type silica connectors; devices with conical bores into which polymer-coated capillary is inserted, finding purchase and seal at some point within the conical bore where the connector inner diameter matches the capillary outer diameter. The press-fit type connectors are typically 4 cm long and the guard column capillary is typically 0.5 m to 1 m long. Non-volatile contaminants within the sample absorb to the bare guard column wall rather than contaminate the more costly separation column. FIG. 5 depicts a replacement for prior art guard columns where the press-fit type connection afforded by a conical bore 53 within the silica support tube 50 that houses a helical monolith 52, double helix monolith or other pattern for various degrees of tortuosity and surface area to volume ratios. Ease of installation is afforded as a previously installed separation column may simply be cut near the injection port with ends inserted into the openings 54 of the device until snug. Sample and carrier gas then enter the guard column port 52 through the remaining conical bore 53, efficiently trapping contaminants before they reach the separation column. The entire package requires no more space than the two press-fit type connectors required for prior art and halves dead volume introduced by use of such connectors. A 1-meter guard column may be replaced by a very short and transparent helical monolith type device that is easier to install, more effective in removing damaging particulates, indicative of exhaustion (by color change with contamination) and more rugged than the traditional, flexible capillary to the point that it may be practical to clean spent monolith guard columns for reuse.

Figure 9:
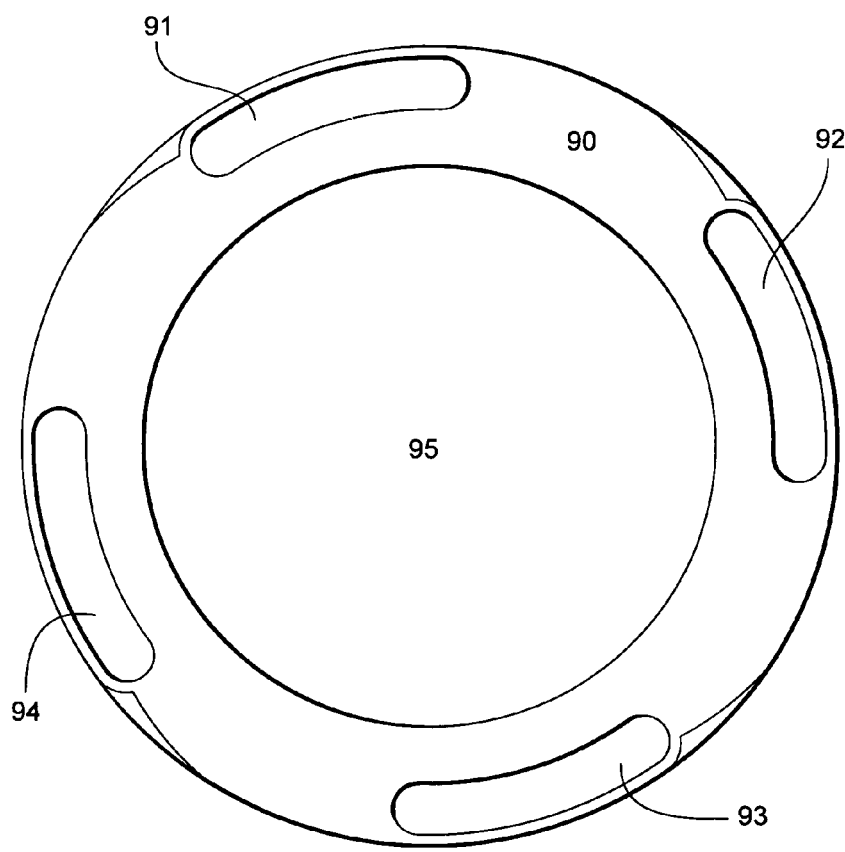
FIG. 9 is an end view in partial section of a possible multilumen capillary structure in a single monolith: four parallel helices.

Alternative means of controlling surface area to volume ratios as well as providing the option for multiple, separate channels in a single monolith are afforded by producing more than one helical channel in the same monolithic structure, as depicted in FIG. 9. In the figure, four separate but parallel and equivalent channels 91, 92, 93 and 94 are formed within the wall 90 of a silica tube defining a central open space 95 that may be used for imaging the channels, bulk fluid movement, etc. or may exist merely for weight reduction in the final device, or may not be present at all (solid rod substrate alternative). It should be apparent that the four individual channels depicted in FIG. 9 may also be interconnected as desired.

FIG. 10 depicts another means of providing multiple separate channels in a single monolith. Here the two channels 104 and 105 are on different diameters within the monolith 100, formed simply by adding a second helical channel onto a previously formed single channel monolith. Openings to the inner 101 and outer 102 channels may be arranged to be separated by a maximum distance on the end plane of the structure, as depicted in the figure, or they may be formed to essentially coincide, enabling individual or tandem address.

FIG. 11 depicts a further strategy for separating channels in monoliths wherein the inner helical channel 115, formed within the wall of rod 110, is channeled again and sealed by fusion of a thin-walled tube 117 over the grooved monolith, forming a second channel 116 of slightly helix diameter. The thin walled tube 117 that defines the outer channel 116 is shorter than the overall rod monolith 110, such that the opening 112 of channel 116 occurs on the cylindrical wall of the structure whereas the opening 111 of the inner channel 115 occurs on one end of the roughly cylindrical structure. The exits for the independent channels may also be similarly separated in space or may occur as depicted, on the same plane of the monolith at 113 and 114. As before, the overall monolith may be a cylindrical solid as depicted, or a hollow cylinder as depicted in FIG. 9.

Figure 14:
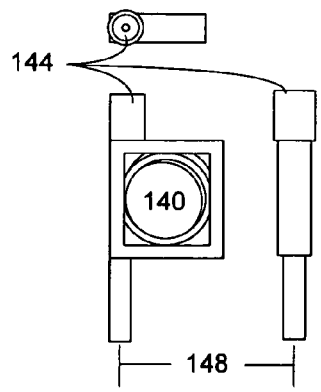
FIG. 14 depicts a prior art capillary module for addressing MTPs.
Figure 19:
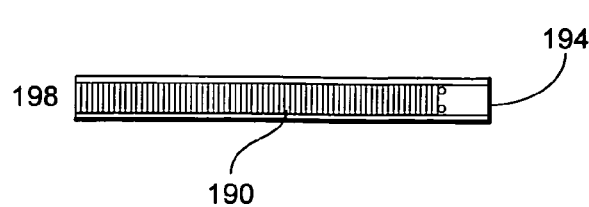
FIG. 19 depicts a perspective view of a micro pipette designed for immobilization of delicate structures like single cells.

In CE type applications, column physical length compression is more dramatic and overall dimensions may be reduced as a consequence. Where coiled capillary devices, FIG. 14, are too cumbersome to be used to address more than one column or row of a 96-well MTP at a time, for example, identical column volumes are provided by short, rigid section of helical in diameters compatible with simultaneous address of each well in up top 1536-well count or high MTPs. FIG. 19 depicts such a replacement monolith where the helical passage 190 is the analog to the coiled capillary in FIG. 14 (140), 194 is an analogous instrument communication well to that of 144 and 198 is the communication end of the device, analogous to the free, flexible capillary end 148 in the prior art.

Moreover, multiple parallel helical channels ending at different points on a monolith (FIG. 11), or in different layers on monoliths (FIG. 12), can perform different tasks simultaneously. For example, though repeated aspiration and expulsion within a well, several target molecules can be selectively and separately extracted without interference and with minimal species loss (high extraction efficiency).

Figure 12:
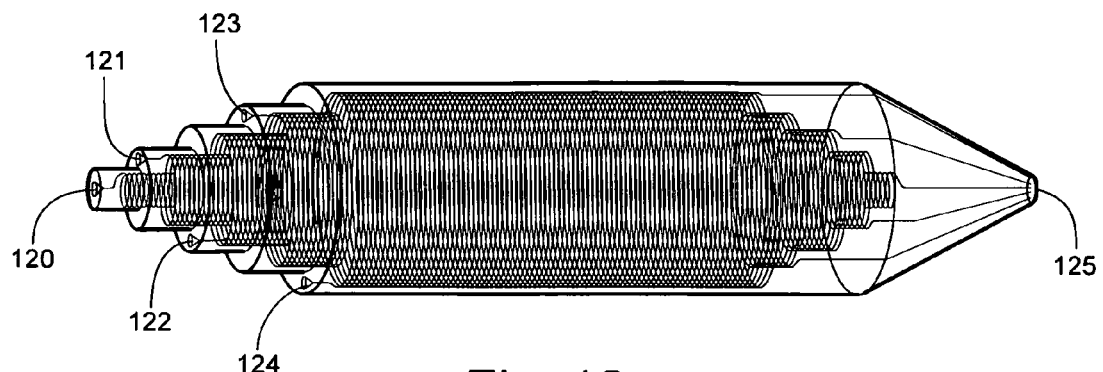
FIG. 12 is a perspective view of a possible means of differential address for each channel in a multilumen monolith where each channel is in a different layer.

FIG. 12 depicts a five-channel device where 120, 121, 122, 123, 124 are the individual channel openings for communication with the instrumentation and 125 is reduced diameter plane with closely spaced openings for communication with the bottom of a microwell. Isolated species could subsequently be eluted sequentially, or in parallel, or in any combination for further study. One channel can add fluid to a well while another removes fluid. A hollow cylinder monolith with an optical fiber or fibers within the bore or a monolith with axial channels in one layer can deliver and receive light from a well while other operations are ongoing or as a separate function, e.g. one could monitor the complete removal of a precious compound with serial rinses without any mechanical motions at all.

Figure 13:
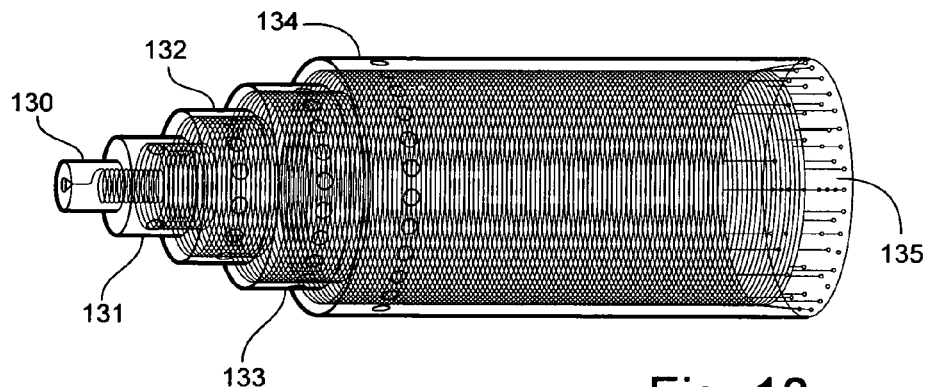
FIG. 13 is a perspective view of an alternative method of providing individual fluidic connections to multiple channels in multiple layers.

FIG. 13 depicts a multilayer monolith design that presents 61 channels of equivalent volume in a single structure, each individually addressable, fluidically and electrically. There is a central, single helical channel with a central port 130. The second layer 131 contains parallel helices with equivalent volume to the central helix, in this case, four channels. The third layer 132 contains eight parallel helical channels while the fourth 133 and fifth 134 contains sixteen and thirty-two, respectively, for a total channel count of sixty-one. Such a structure can be produced in dimensions compatible with high count MTPs with individual openings at the well communication plane 135.

By way of example, where a sixteen by twenty-four array of devices such as depicted in FIG. 13 can be assembled in 4.5 mm centers, sixty-one target proteins in each well could be isolated within separate channels without splitting the samples. One scenario for massively parallel isolation and study of macromolecules in a 384-well MTP is: immerse the array in the wells, pull samples into the capillaries containing WCOT affinity coatings for the target proteins, expel the sample and repeat several times until statistics indicate diminishing return (likely no more than about 60 cycles to extract ~90% of target proteins in each well), remove the array, load a eluting solution plug into the channels, draw it back and forth through the channels several times to release most of the protein into solution within the plugs, load buffer behind the plugs and move it forward to the flat output face of the monolith and sequentially expel each plug onto a compact disk (CD) type target or into new wells for subsequent analysis. Expulsion of the individual proteins may be accomplished through application of high voltage to the opposite end of the capillaries, in sequence or in groups, to expel isolates precisely to targets held at a lower potential or ground. The total number of proteins that may be isolated, concentrated and deposited by this single, automated plate-sampling device is 23,424. Electrical connections to each channel bore may be made through thin film gold contacts within the conical openings or other means. An imprinted CD-type target could be loaded into a mass spectrometer (MS) for sequential matrix assisted laser desorption ionization (MALDI). Alternatively, the individual monoliths may be loaded into an electro spray ionization (ESI) source on a MS for direct elution-ionization. Other potential elution schemes will be apparent to those skilled in the art. With the electric expulsion method, it is completely unnecessary to make individual fluidic connections to each channel for isolating the target molecules if accurate fluid metering is employed and the eluent and buffer are compatible with all of the chemistries in a single monolithic multichannel capillary, greatly simplifying instrument and monolith design.

This realistic scenario represents an approximate 2000-fold increase in throughput with respect to current art (maximum of 12 protein affinity tips reading one row of a 96-well MTP at a time). This improvement may be fundamentally enabling for acquiring the data necessary to understand the human genome/proteome/metabalome, or human biological systems problem, within a time frame that is compatible with financing such a project. Were one to produce a five-layer structure with larger capillary counts, e.g. 1, 4, 16, 64, 256 for a 341-channel monolith, compatible with larger well count MTPs, e.g. 32 by 48 or 1536 wells, over one half of a million target molecules may be isolated and concentrated in a matter of minutes, in a fully automated system. This represents an increase of 43,648-fold over current art and is likely possible to accomplish with the art disclosed herein.

For applications where individual channels need not be individually connected to the instrument (as discussed above), relatively long sections of the monolithic, multilumen capillary columns could be produced with individual channel chemistries applied at the full length, for subsequent sectioning into multiple modules for automated array assembly. Costs for individual protein isolation and concentration might well be reduced by similar orders of magnitude as the parallel throughput increase, e.g. a three-order reduction in costs is not an unreasonable expectation.

Figure 18:
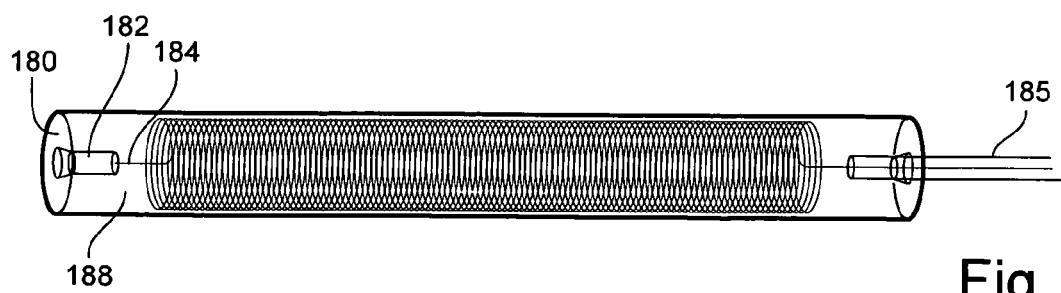
FIG. 18 depicts a partial section of a separation and concentration capillary compatible with address of all wells of high count MTPs.

In that the silica structures are laser fused, with no conductive contaminants, high voltage may be applied across the various lumen for CE-type separations. Additional separation dimensions may be enabled through the tortuosity and variable surface area to volume aspects of the devices and by surface modifications performed before or after fusion encapsulation. Numerous, convenient fluidic connection schemes may be envisioned. FIG. 18 illustrates one such simple connection scheme where electrical connection may be provided through thin layer circuits printed directly on the monolith OD 188 and in the capillary mating channels 182 and within the very bore itself 184, or by use of plated capillary for interface 185.

As there is no requirement for a protective polymer coating on the relatively rugged monolithic columns, optical detection methods may be preformed anywhere along the length of the channels or all along the length of the channels and illumination or excitation may come from within the central channel through use of a lateral emission fiber optic or along the monolith axis (which may be clad with polymer or doped silica to form a cylindrical waveguide) or at specific points through specific structures provided on the monolith for that purpose, as embedded optical fiber or observation windows.

Cumbersome, costly and fragile capillary arrays need not be limiting in massively parallel screening applications. Monolith arrays, designed to accurately address MTPs are easily integrated to robotic systems for rinse and reuse, thorough cleaning, or replacement. Costs of producing flexible capillary arrays are essentially eliminated, as individual monoliths as well as assembled arrays are robot-compatible where flexible arrays are not, and must be hand made and installed by skilled technicians. The cost of the materials and equipment required to produce the new art monolithic devices is equal to or substantially less than that for traditional capillary so overall applications costs are greatly reduced, permitting disposable devices that eliminate cross-contamination issues. Again, thin film gold circuits on the outer diameter of the monolith can make individual and common connections to channels within single and even multiple lumen devices.

While the costs for producing complex microfluidic circuit devices (aka, bioMEMS, lab-on-a-chip, biochips) are somewhat higher than single channel devices for addressing MTPs, such fabrication is easily orders less costly than current methods and is compatible with mass production through automation; changing circuit patterns and dimensions is simply a matter of changing the programmed motion code for the laser scribing system. FIG. 15 depicts a helical monolith analog to the most common, and simple, CE-chip type device where 150 and 151 are the buffer/electrode ports, holes, 155 and 156 popped in the side of the structure serve as sample introduction port and waste, respectively, communicating with the separation channel via open sections of an otherwise closed helical channel 152 that is formed by adding links 153 in a staggered manner to produce the sampling "loop" 154. It is envisioned that devices of a standardized port configuration, with very different circuits and applications, could be produced with identifying markers (such as conductive paths or bar codes). By simply dropping the cylinder into an instrument, the device type is recognized the instrument configures itself for proper operations without additional operator input. In such a manner, disposable fluidic circuit devices for monitoring myriad environmental elements, biological metabolites, genetic codes, etc. need not be instrument specific: to monitor for A, B and C only insure monolith A, B and C are presented to an instrument bank. Random sampling is thus facilitated, enabling fully automated Monte Carlo type methods in sampling for diverse substances.

In addition, microscale versions (or drawn taper versions) of such multiple channel devices may be used (a) in reduced stress immobilization applications, (b) as microfilters (sieves) and (c) in retaining materials within microcolumns.

Figure 17:
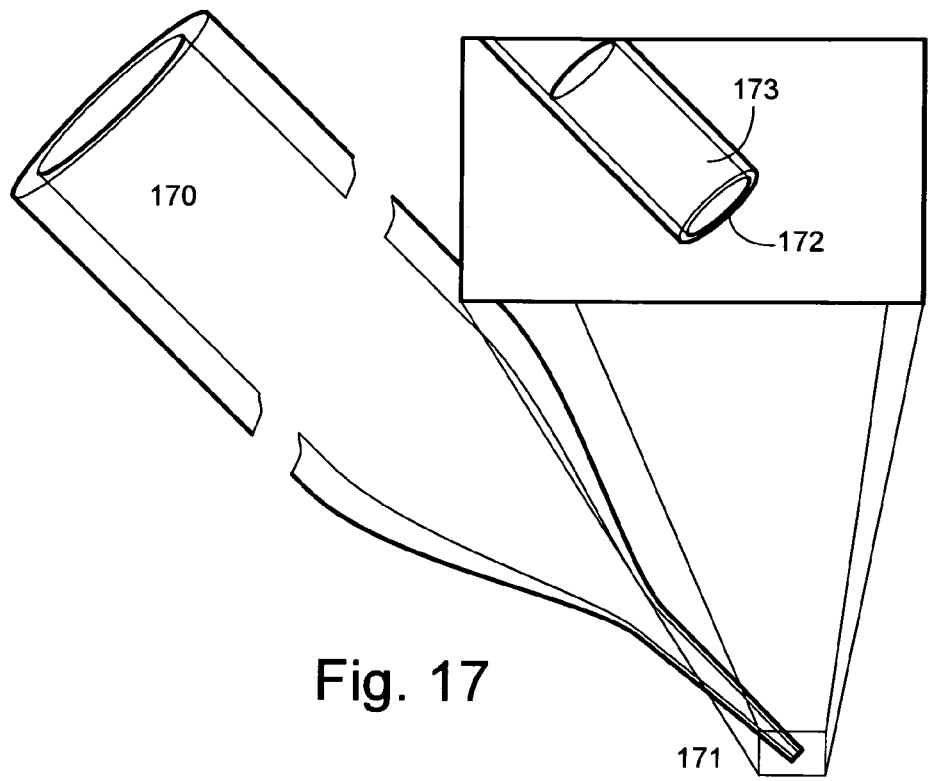
FIG. 17 is a perspective view with expanded detail of a cell immobilization pipette based upon the new art.

By breaking a force into multiple, smaller subunits within the scaffold defined by the walls separating the channels in a multilumen monolith, the possibilities for applying damaging force to delicate cell walls are reduced and immobilization may be more secure. For example, a multichannel pipette a tip, as opposed to single channel devices, may immobilize a cell for cellular surgery by suction at the tip of a drawn helical monolith tipped pipette (FIG. 17). In addition, one or more lumen of drawn multilumen pipettes may be used for purposes other than immobilization. during immobilization, e.g. extraction or delivery of materials or measurement of fluorescence or electric potential. FIG. 17 depicts a basic multilumen sieve-equipped pipette where a capillary of original bore 170 is drawn to smaller diameter 171 (alternatively, a commerical pipette may be used). A plug of multilumen capillary 172 is fused to the thinned wall 173 of the original pipette, forming a filter for use in applications such as ESI-MS or mechanism for distribution of pressure differentials for applications such as cell immobilization of for nebulization, etc.

Sintered frits formed within capillary are notoriously problematic. Aside from being difficult to form reproducibly, the flow restriction within tiny bores is often unacceptably high. Frit breakup, clogging and irreversible retention of target molecules are common problems. In CE application, such flow restriction can cause damaging Joule heating due to increased electrical resistance. Clogging is the principal lifetime-limiting failure in ESI-MS capillary. Drawn multilumen sections can be made with very little flow restriction to very high flow restriction—well beyond the limits for each provided by frits. Prepared plugs may be easily fused within capillary bores or, in that sample crossover between independent channels within a monolith is impossible, larger sleeves containing sieves can simply be glued into place without concern for infiltration beyond the sieve channels in communication with the capillary bore.

Those skilled in the art will readily recognize additional variations of value, such as the formation of precise nozzles at capillary channel tips for piezoelectric or other pressure or aspiration mediated delivery of isolated products from channels. Finally, additional applications for the technology disclosed here are also apparent, but untested at this time, e.g. in fast automated injection for GC, discrimination of sample component species is problematic with current art injection port liners, primarily due to the Leidenfrost effect (solvated sample failing to vaporize due to lack of contact with the heated liner wall). A macroscale multiple helix capillary column plug placed in an injection port liner might provide a solution by accelerating solvated sample in vortex flow to force intimate contact with the liner wall well before the capillary inlet.

Similarly, non-classical chemical analysis applications for controlling fluid and gas flows are envisioned.

The preferred embodiment of the invention is described above in the Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

The invention claimed is:

1. A method for forming a capillary column comprising the steps of providing a glass rod, scribing a recessed pattern on an exterior surface of the glass rod by focusing and indexing at least one laser along the axis of the rod while the rod is under rotation, providing a thin walled glass sleeve that is slightly larger in bore than the glass rod, inserting the patterned glass rod within the glass sleeve and fusing the glass sleeve to the exterior surface of the glass rod while not filling in the recessed pattern by rotating the assembly and defocusing the laser focal point to a location than on the assembly outer diameter so as to just melt a portion of the thin walled glass sleeve that is adjacent non-recessed portions of the glass rod and fusing the melted portion of the thin walled glass sleeve to non-recessed portions of the glass rod, thereby defining a capillary column in the shape of the recessed pattern.

2. The method according to claim 1 wherein the at least one laser is selected from the group comprising $CO_2$, CO, YAG, YIG and Excimer lasers.

3. The method according to claim 1 wherein the glass rod is a fused quartz, a fused silica, a doped fused silica, sapphire, a ceramic or a compound glass.

4. The method according to claim 1 wherein the recessed pattern is a single helical channel, a multiple parallel helical channel, a multiple serial helical channel, a multiple mixed serial and parallel helical channel, crossed helical channels or a non-helical channel.

5. A method for forming a capillary column comprising the steps of providing a glass tube, scribing a recessed pattern on an exterior surface of the glass tube by focusing and indexing at least one laser along the axis of the tube while the tube is under rotation, providing a thin walled glass sleeve that is slightly larger in bore than the glass tube, inserting the patterned glass tube within the glass sleeve and fusing the glass sleeve to the exterior surface of the glass tube while not filling in the recessed pattern by rotating the assembly and defocusing the laser focal point to a location than on the assembly outer diameter so as to just melt a portion of the thin walled glass sleeve that is adjacent non-recessed portions of the glass tube and fusing the melted portion of the thin walled glass sleeve to non-recessed portions of the glass tube, thereby forming a capillary in the shape of the recessed pattern.

6. The method according to claim 5 wherein the at least one laser is selected from the group comprising $CO_2$, CO, YAG, YIG and Excimer lasers.

7. The method according to claim 5 wherein the glass rod is a fused quartz, a fused silica, a doped fused silica, sapphire, a ceramic or a compound glass.

8. The method according to claim 5 wherein the recessed pattern is a single helical channel, a multiple parallel helical channel, a multiple serial helical channel, a multiple mixed serial and parallel helical channel, crossed helical channels or a non-helical channel.

* * * * *